United States Patent [19]

Simion et al.

[11] Patent Number: 5,480,633
[45] Date of Patent: * Jan. 2, 1996

[54] MILD CLEANSER AND CONDITIONER TO YIELD SOFT SMOOTH SKIN

[75] Inventors: Frederick A. Simion, Hazlet; Robert H. Cagan, Lawrenceville; Linda D. Rhein, Somerville; John C. Blake-Haskins, Piscataway; Stephen W. Babulak, Kendall Pk., all of N.J.

[73] Assignee: Colgate-Palmolive Company, Piscataway, N.J.

[ * ] Notice: The portion of the term of this patent subsequent to May 9, 2006, has been disclaimed.

[21] Appl. No.: 126,751

[22] Filed: Sep. 27, 1993

Related U.S. Application Data

[63] Continuation of Ser. No. 751,860, Aug. 29, 1991, abandoned, which is a continuation of Ser. No. 128,013, Dec. 2, 1987, abandoned.

[51] Int. Cl.$^6$ ............................... A61K 7/06; A61K 9/08
[52] U.S. Cl. .................. 424/70.1; 424/70.31; 424/73; 252/142; 514/772.6; 514/784; 514/788; 514/844; 514/846; 514/847; 514/873; 514/944; 514/975
[58] Field of Search ................... 424/73, 70.1, 70.31, 424/70.11

[56] References Cited

U.S. PATENT DOCUMENTS

| | | | |
|---|---|---|---|
| 3,915,633 | 10/1975 | Ramachandran | 8/137 |
| 4,323,468 | 4/1982 | Grollier et al. | 252/174.17 |
| 4,828,750 | 5/1989 | Simion et al. | 252/142 |

Primary Examiner—Thurman K. Page
Assistant Examiner—James M. Spear
Attorney, Agent, or Firm—Colgate-Palmolive Company

[57] ABSTRACT

A skin cleanser and conditioner composition and particularly a facial rinse that removes soap and surfactant residue from the skin and thereby prevents irritation caused by the deposition of soaps and surfactants thereon, consisting of low levels of a nonionic surfactant, low levels of an organic acid such as citric acid/sodium citrate, and a major amount of water, which composition may be in the form of a liquid or gel.

53 Claims, No Drawings

MILD CLEANSER AND CONDITIONER TO YIELD SOFT SMOOTH SKIN

This application is a continuation of application Ser. No. 7/751,860 filed Aug. 29, 1991, now abandoned which is a continuation of Ser. No. 7/128,013, filed Dec. 2, 1987, now abandoned.

FIELD OF THE INVENTION

This invention relates to an aqueous skin rinse formulation for soap and surfactant residue removal consisting of a minimal amount of a water soluble nonionic surfactant such as the polyethylene oxide—condensates of higher fatty alcohols, and a polysorbate containing 20 moles of ethylene oxide, a minimal amount of an organic acid having a pKa of 4.5 to 6.5 and/or a monovalent cation salt of the acid, and a major amount of water in an amount of about 84–98% by weight of the liquid formulation having a pH within the range of about 4.5–6.5. This product may be used as a skin cleanser, as an after-rinse, i.e. after the soap lather is rinsed from the face, or as a preshave/skin conditioner to prevent or reduce the deposition of shaving cream soap on the skin. The present facial rinse has the dual function of removing substantially all the residual soap and surfactant residue or preventing the deposition of soap and/or surfactant, and simultaneously conditioning the skin to feel soft, smooth and moisturized.

BACKGROUND AND PRIOR ART

Soap and surfactant residue which is retained on the skin after facial washing there-with has been shown to cause skin roughness, tightness and dryness. Surfactants such as alkyl ether sulfates, alkyl sulfates, alkyl benzenes sulfonates, and even amine oxides are potential skin irritants. Patch tests therewith confirm that they have the potential to irritate skin.

For a surfactant to have a negative effect on the skin, it may have to be absorbed to, and be retained on, the skin after washing. Indeed Imokawa and Mishima (Nahihi Kaishi 86 473–481 (1976)) showed that skin roughness was related to surfactant deposition. In studying the skin feel effects of surfactant deposition, soap was precipitated onto the skin by adding calcium and magnesium salts to the wash water (i.e. increasing water hardness).

In a clinical study using several consumers who washed their faces with a leading brand of soap in hard water (400 ppm), deionized water and soap, and hard water without soap, and deionized water without soap; it was demonstrated that facial washing with a leading brand of soap in hard water caused significantly more perceived tightness than washing with soap in deionized water. (Washing with soap and deionized water elicited some perceived tightness). No tightness or other skin feel characteristic was felt with either the hard water or deionized water without the soap. This study demonstrated that washing with soap generates tightness of the skin.

An in vitro study using wool fabric and laurate soap demonstrated that Ca++ and Mg++ salts that produce water hardness increase surfactant deposition and absorption of the soap to the wool fabric, a keratin substrate. Hence, the water hardness increases the binding of the laurate soap to wool and, by analogy to skin, decreases the ability to wash the soap off the wool or skin, which binds the soap surfactant in a manner similarly to wool. It is the removal of this soap residue from the skin which is one aspect of the subject matter of present invention.

Commercial facial cleansers, such as Noxema which is a white cream, and Olay Beauty cleanser, contain soaps as ingredients in their formulations which exacerbate the irritation problems associated with soap residues on the skin. The removal of soap residues after cleansing with soap has not been addressed in the prior art. However, moisturizers have been used to mask the negative skin sensations after washing with soap.

The prior art discloses assorted liquid cosmetic lotions for cleansing purposes, as disclosed in U.S. Pat. No. 3,011,950, wherein a minor amount of a nonionic or anionic surfactant is dissolved in the aqueous phase containing a water soluble polymer and an inert gas such as oxygen, nitrogen or compressed air, dispersed therein to give a sparkling effect. U.S. Pat. No. 4,323,468 discloses a make-up remover composition for face and eyes comprising an oil in water emulsion containing a nonionic, anionic or cationic surfactant, an extract of sarsaparilla, a preservative, and a citrate or phosphate or lactate buffer to maintain a pH of 4–8.5 and preferably 6–8. U.S. Pat. No. 4,533,545 discloses cosmetic compositions containing polyethylene glycol derivatives as thickeners in the presence of a nonionic, anionic, cationic or amphoteric surfactant. U.S. Pat. No. 3,956,951 discloses a method of shaving which comprises washing the face with soap and water, rinsing all the soap from the face, and rubbing the wetted skin with a water-soluble solid polyethylene oxide polymer wafer prior to shaving with a blade type razor. U.S. Pat. No. 4,412,943 discloses a shampoo containing an alkyl sulfate, ethylene diaminetetraacetate salts, and an acid such as citric acid. U.S. Pat. No. 3,748,276 discloses aqueous gel compositions for use in cosmetics containing a polyether polyol gelling agent. U.S. Pat. No. 4,140,656 discloses an anhydrous clear gel facial cleanser for removal of eye make-up containing mineral oil, phosphate esters and carboxy vinyl polymers such as a polymer of acrylic acid crosslinked with polyalkylene polyether (Carbopol by B. F. Goodrich Company). U.S. Pat. No. 4,360,451 discloses amphoteric surfactant gels containing an amphoteric surfactant, a polyoxybutylene—polyoxyethylene block copolymer, and water for use in facial cleansing bath and shower gels, shampoos and the like.

None of the prior art cosmetic compositions have addressed adverse skin effects of the soap residue retained on the skin, particularly the face, after washing with soap and water.

It has now been found that a liquid skin cleanser, particularly a facial rinse/skin conditioner formulation effective in removing both soap and surfactant residue from the skin and reducing skin irritation and negative sensations of skin dryness, roughness and tightness, consists of low concentrations of a nonionic surfactant as the sole surfactant, and an organic acid (or salt thereof) such as citric acid to adjust the pH to that of the human skin (4.5 to 6.5), and a major amount of water, preferably deionized water; which may be thickened with polyethylene glycol—150 distearate to a thick liquid or thickened with an acrylic acid polymer to form a gel, and preferably contains a preservative. One such material comprises 1,3-dimethylol-5, 5 dimethyl (DMDM) Hydantoin and disodium ethylene diaminetatraacetate (EDTA). Another is Germaben II, a product of Sutton Laboratories, Inc.

The use of a nonionic surfactant as one of the ingredients in a liquid detergent for cleaning fabrics is well known in the prior art as disclosed in U.S. Pat. Nos. 3,764,544; 3,959,163; and 4,206,070.

U.S. Pat. No. 3,915,633 discloses an aqueous prewash aerosol spray soil release composition for use with a detergent or soap in a laundering operation, consisting of 1–20% by weight of an organic acid, i.e. citric acid, 2–30% by weight of an anionic or nonionic surfactant, water and an aerosol propellant. Canadian Patent No. 1,086,178 discloses a liquid heavy duty laundry detergent composition containing 20–70% by weight of a soluble ethoxylated nonionic surfactant, 0.1–1.25% by weight of a polyacid, i.e. citric acid, and water/organic solvents, having a pH of 6–7.5.

Also disclosed in the prior art are mixtures of a nonionic surfactant and polyacrylate thickeners in aqueous dishwashing detergent formulations as disclosed in U.S. Pat. Nos. 3,950,260 and 4,226,736.

U.S. Pat. No. 4,501,680 discloses acidic liquid detergent compositions for cleaning ceramic tiles without eroding grout between them, comprising a minor proportion of glutaric acid and a lesser amount of phosphoric acid to provide a pH of 3–5, a minor amount of an ethoxylated fatty alcohol, a minor amount of a diethylene glycol monoalkyl ether, and a major amount of water.

U.S. Pat. No. 4,172,140 discloses an antimicrobial composition for inhibiting the growth of microorganisms in an aqueous fluid medium comprising as the active ingredients, an admixture of 1,3-dimethylol-5,5 dimethyl hydantoin and disodium ethylene diaminetetraacetate, for use in metal working fluids, cutting oil fluids, coolants, lubricants, and the like.

None of the aforesaid prior art discloses a skin cleanser and skin conditioner or a pre or post-shave/skin conditioner consisting of a low level of a nonionic surfactant as the sole surfactant, a minor amount of an organic acid (or salt thereof) having a pKa from 4.5 to 6.5 to provide a pH of about 4.5 to 6.5, and a major amount of water, which may be thickened with polyethylene glycol— 150 distearate to a thick liquid or thickened with an acrylic acid polymer to form a gel, and preferably contains a preservative system.

SUMMARY OF THE INVENTION

It has been found that the soap and surfactant residue retained on the skin after facial washing with soap causes skin damage such as dryness, roughness or tightness. It has additionally been found that the soap residue can be effectively removed from the skin with the present novel cleanser formulation consisting of a minor amount of a water soluble nonionic surfactant, with the pH adjusted to that of human skin, using an organic acid having a pKa from 4.5 to 6.5 and a major amount of water, preferably deionized water. The novel cleansers are clear products with viscosities ranging from watery solutions to thick gels, by the addition of a viscosity control agent selected from the group consisting of a diester of stearic acid and polyoxyethylene (PEG 150 distearate), and a polyacrylic acid resin (Carbopol 941). Compositions prepared with either thickener yield soft, smooth skin, similar to the unthickened watery solution, without leaving a slimy or tacky feeling. The present novel composition functions as a skin cleanser and conditioner, a facial rinse, and as a pre-shave and post-shave skin conditioner which will reduce the deposition of shaving cream soap on the skin and remove soap residue from the skin.

This invention permits consumers to clean themselves with soap, without experiencing the skin effects that consumers associate with skin damage such as dryness, roughness or tightness. This invention represents an improvement over applying moisturizers to the skin, since it removes the irritating species (soap), rather than mask negative sensations (e.g. dryness). Unlike moisturizers, using this product does not leave a greasy film on the skin after usage.

Accordingly, a primary object of the present invention is to provide a liquid skin cleanser and conditioner composition to remove soap and surfactant residue from the skin and thereby prevent irritation due to soap and surfactant.

Another object of this invention is to provide a facial rinse/skin conditioner, to be used after washing with soap and water, which results in a soft, smooth and moisturized feel on the skin.

Still another object of this invention is to provide a skin rinse/skin conditioner containing as the major ingredients, a nonionic surfactant, an organic acid, a major amount of water, and having a pH adjusted to that of human skin.

Another object of this invention is to provide a clear liquid skin cleanser, facial conditioner/rinse, a pre-shave/skin conditioner or a post-shave rinse with viscosities ranging from watery solutions to thick gels.

Another object of this invention is to provide a thickened or gelled skin cleanser and conditioner particularly a facial cleanser/skin conditioner containing a diester of stearic acid and polyoxyethylene or a polyacrylic acid resin as the thickening agent.

Still another object of this invention is to provide a skin conditioner which does not leave a greasy film on the skin after usage.

Another object of this invention is to provide a skin cleanser and conditioner or pre-shave/skin conditioner also containing a preservative system.

Additional objects, advantages and novel features of the invention will be set forth in part in the description which follows, and in part will become apparent upon examination of the following specification or may be learned by practice of this invention.

To achieve the foregoing and other objects in accordance with the present invention, as embodied and broadly described herein, the novel liquid skin cleanser and conditioner composition to remove soap and surfactant residue from the skin, of this invention, consists essentially of a major amount of water preferably deionized water, about 0.25–6% by weight of a nonionic surfactant as the sole surfactant, about 0.05–5% by weight of an organic acid having a pKa from 4.5 to 6.5 or a monovalent cation salt of the acid or a mixture of said acid and salt, said composition having a pH of 4.5–6.5 and preferably 5–6.

More specifically, the clear liquid cleanser/skin conditioner composition of the present invention, which removes soap and surfactant residue from the skin and simultaneously conditions the skin, consists essentially of about 84–98% water; about 0.7–6% by weight of a water-soluble ethoxylated nonionic surfactant, as the sole surfactant, selected from the group consisting of a polyethylene glycol ether condensate of a $C_8$–$C_{20}$ fatty alcohol or mixture of fatty alcohols with an average of 5 to 30 moles of ethylene oxide, and a polysorbate having an average of 20 moles of ethylene oxide; about 0.1–2% by weight of an organic acid, and/or sodium salt of the acid to adjust the pH of the compositon to about 5–6; about 0.5–4% and preferably 0.6–2% by weight of a thickening agent selected from the group consisting of a diester of stearic acid and polyoxyethylene, and a polyacrylic acid resin; and a preservative system, which might comprise 1,3-dimethylol-5,5 dimethyl hydantoin and disodium ethylene diamine-tetraacetate in equal amounts, or Germaben II.

The skin cleanser of the present invention is preferably thickened to increase consumer acceptability by using the polyacrylic acid resin to form a gel, or the diester of stearic acid and polyoxyethylene to form a thick liquid.

The preservative systems in the present novel compositions effectively preserve the product against bacteria such as *B. subtilis*, and mold.

The skin cleanser of the present invention removes soap and surfactants, as well as dirt, oil, and other traditional soils from the skin without irritating the skin and face.

The formulations in accordance with present invention can also be used to remove soap from other surfaces that contain keratins, or similar proteins, such as hair, wool, cotton and other fabrics.

Present novel formulations may be used to remove other surfactants from wool and other surfaces.

DETAILED DESCRIPTION OF THE INVENTION

The major essential component in the liquid skin cleanser and conditioner compositions of the present invention is about 84 to 98% by weight water, preferably deionized water. The water component is essential in the preparation of the present stable mild facial cleansers and functions as a solvent or vehicle for the other active ingredients in the composition, which are capable of being readily rinsed from the skin. The water component does not attribute negative sensations to the skin.

Another essential ingredient in the present skin cleanser is a water-soluble nonionic surfactant, as the sole surfactant, preferably an ethoxylated nonionic surfactant selected from the group consisting of a polyethylene glycol ether condensate of a $C_8$–$C_{20}$ fatty alcohol or mixture of fatty alcohols with an average of 5–30 moles of ethylene oxide, and a polysorbate containing 20 moles ethylene oxide. Suitable fatty alcohols preferably contain 9 to 18 carbon atoms and most preferably 11 to 15 carbon atoms. Typical examples are lauryl, tridecyl, myristyl, cetyl, stearyl and oleyl alcohols or mixtures thereof, which may be condensed with about 5 to 20 moles ethylene oxide. Typical commercial products are the Tergitols obtainable from Union Carbide. More specifically, Tergitol 15-S-9 is a polyethylene glycol ether of a mixture of synthetic $C_{11-15}$ fatty alcohols with an average of 9 moles of ethylene oxide. Tergitol 25-L-7 is a polyethylene glycol ether of a mixture of synthetic $C_{12-15}$ fatty alcohols with an average of 7 moles of ethylene oxide.

The polysorbates are condensates of polyethylene oxide with fatty acid esters or mixtures of fatty acid esters of sorbitol and sorbitol anhydride. Fatty acid esters include laurate esters, stearate esters, palmitate esters or oleate esters. The fatty acid esters of sorbitol and sorbitol anhydride are preferably condensed with 20 moles of ethylene oxide. Typical products are Tweens obtainable from the Atlas Company, also known as Polysorbates. More specifically, Polysorbate 20 (Tween 20) is a mixture of laurate esters of sorbitol and sorbitol anhydrides, consisting predominately of the monoester, condensed with about 20 moles of ethylene oxide, commonly known as Polyoxyethylene (20) Sorbitan Monolaurate. Polysorbate 80 (Tween 80) is a mixture of oleate esters of sorbitol and sorbitol anhydrides, consisting predominantly of the monoester, condensed with about 20 moles of ethylene oxide, commonly known as Polyoxyethylene (20) sorbitan monooleate. The nonionic surfactant constitutes about 0.25–6%, preferably about 0.7–6%, and most preferably 0.5–2% by weight of the composition. The minimal amount of nonionic surfactant necessary for the aqueous rinse base to adequately remove bound soap is shown in Table I.

Wool keratin was used as a good substitute for human stratum corneum to quantitively compare the removal of residual soap from a skin-like substrate with various rinse treatments. Wool keratin was pretreated with a solution of radiolabelled soap, rinsed with hard water to remove loosely bound soap, and then treated with various rinse formulations. The amount of soap removed from the keratin is determined by analyzing the rinse solutions and wool for radioactivity.

Rinse formulations were prepared containing 2.0% citric acid, and nonionic surfactant (Tergitol 15-S-9) varying in concentration from 0 to 2.0%. All solutions were adjusted to pH 5.0. The results shown in Table I indicate that in the absence of surfactant, less than 20% of the residual soap is removed. The addition of even a small amount of surfactant increases the removal to almost 90%, and that a maximum in residue removal is reached at about 2.0.%. These results show that nonionic surfactant is necessary for the rinse base to adequately remove bound soap, however the amount needed for almost complete removal is relatively low.

TABLE I

| Effect of Surfactant Concentration on Residual Soap Removal by a Rinse Formula | |
|---|---|
| Treatment* Removal | Percent Soap |
| 0% Tergitol | 17.9 ± 1.10 |
| 0.25% Tergitol | 87.0 ± 2.34 |
| 0.50% Tergitol | 91.4 ± 0.38 |
| 0.75% Tergitol | 89.5 ± 0.80 |
| 1.00% Tergitol | 92.9 ± 1.66 |
| 2.00% Tergitol | 96.4 ± 0.31 |

*All treatment solutions contained 2% citric acid, adjusted to pH 5.0

Another essential ingredient in the present facial cleanser/skin conditioner is an organic acid having a pKa value from 4.5 to 6.5, a monovalent cation salt of the acid, or a mixture of said acid and salt. The preferred acid is citric acid $C_3H_4(OH)(COOH)_3$, or a mixture of citric acid and a citrate salt made with a monovalent cation such as sodium or triethanolamine. The citric acid and/or citrate buffers soap removal from the skin by coacting with the nonionic surfactant in removing soap residue bound to the skin. Other suitable acids include acetic, succinic and glutaric acids. The organic acid constitutes about 0.05 to 5%, preferably 0.1 to 2% by weight of the composition. The minimal amount of organic acid required to buffer soap removal from the skin is shown in Table II, using the pretreated wool keratin as defined above, and the amount of soap removed is similarly determined.

Rinse formulations were prepared containing 0.25% Tergitol, pH 5.0, and citric acid concentrations varying from 0 to 2%. The results are shown in Table II. As can be clearly seen, citric acid is also necessary for adequate residue removal. The rinse base removes only 66% of the residual soap, while addition of the smallest amount of citric acid (0.25%) increases the performance of the product to 88%. The results show a deviation from ideal behavior, in that there is an optimum concentration of citric acid for maximum performance near 0.5%, followed by a decrease in performance as the citric acid concentration continues to increase.

TABLE II

Effect of Organic Acid Concentration on Residual Soap Removal by a Rinse Formula

| Treatment* Removal | Percent Soap |
|---|---|
| 0% Citric Acid | 66.0 ± 5.4 |
| 0.25% Citric Acid | 87.4 ± 0.41 |
| 0.50% Citric Acid | 88.6 ± 0.27 |
| 0.75% Citric Acid | 86.8 ± 1.28 |
| 1.00% Citric Acid | 84.9 ± 1.30 |
| 2.00% Citric Acid | 72.5 ± 6.42 |

*All treatment solutions contained 0.25% Tergitol, adjusted to pH 5.0

A preferred additive in the present skin cleanser is a thickening agent selected from the group consisting of a diester of stearic acid and polyoxyethylene (PEG 150 distearate) and a polyacrylic resin (such as Carbopol 941 or 940 or 1342). Carbopol 940 has rinsibility advantages over Carbopol 941. The Carbopol resins obtainable from the Goodrich Co., as a fluffy, dry powder are water soluble polymers of acrylic acid with a poly/functional agent, also known as polyacrylic acid resins by the CTFA name of Carbomers. Low concentrations of polyacrylic acid resins, about 0.1–4% and preferably about 0.1–2% by weight, effectively thicken the facial cleanser and form a gel facial cleanser which is clear, colorless and flows slowly when poured. However, Carbopol gels lose viscosity when exposed to UV light. Therefore, a UV stabilizer such as benzophenone should be added, especially if the product is sold in a clear bottle. The PEG-150 distearate, in amounts of 0.1–4% and preferably 2–4% by weight, increases the viscosity of the watery solution to a desired thickness, preferaby to a thick liquid.

It has been found that the aforesaid two viscosity control agents provide viscosity control without negative sensory attributes. In small, in-house tests, panelists reported that prototype facial cleansers prepared with either thickener, yielded soft, smooth skin without leaving a slimy or tacky feeling, similar to the use of the unthickened products. It has additionally been found that said two thickening agents enable the formulation of this product to vary within a range of viscosities, from watery solutions to thick gels, while maintaining the clarity as well as the tactile sensations afforded by the unthickened formulations. Other suitable thickening agents capable of maintaining the clarity and the tactile sensations of the unthickened formulations may be also used. However, it has been found that the use of the thickening agents guar gums and cellulose resins are unacceptable from a sensory standpoint. The product containing guar gum resulted in a slimy feel on the skin; and the product containing cellulose thickener resulted in a tacky feel on the skin. Accordingly, the preferred thickening agents are PEG-150 distearate and the polyacrylic resins.

Another additive in the facial cleanser is a preservative system of 1,3-dimethylol-5,5 dimethyl hydantoin (DMDM hydantoin) and disodium ethylene diamine tetraacetate (EDTA), preferably in equal amounts of 0.3% by weight of each component. This preservative system effectively preserves the facial cleanser of present invention against mold and bacteria such as B. subtilis. An aqueous solution of a combination of DMDM hydantoin and EDTA as an antimicrobial composition for inhibiting growth of microorganisms is described in U.S. Pat. No. 4,172,140, the contents of which are herein incorporated by reference. This patent describes the use of a 0.25:1 to 20:1 ratio of DMDM hydantoin to EDTA as a preservative in metal working fluids, cutting oil fluids and other coolants. Another suitable preservative is Germaben II, a product of Sutton Laboratories, Inc., which comprises propylene glycol 50%, diazolidinyl urea 30%, methylparaben 11%, and propylparaben 3%. The Germaben II preservative does not reduce viscosity as much as the combination of EDTA and DMDM hydantoin preservative, so less Carbopol is needed to achieve the same viscosity.

The cleanser conditioner compositions of this invention also may contain minor amounts of conventional additional components to impart any desired characteristic, which are compatible with the facial cleanser formulation, and do not adversely affect its tactile properties and soap removal properties. Suitable additives include slip agents or emollients to the gel cleanser formulation to improve the cosmetic acceptability to consumers, such as polyethylene glycols up to a maximum of 6%, a copolymer of methyl vinyl ether and maleic hydride (Gantrez) up to a maximum of 0.5%, and glycerin up to maximum of 1%. Silicones such as dimethicone copolymer up to a maximum of 2% may be added to the preshave or post-shave skin conditioner to enhance lubrication of the beard and reduce skin damage during shaving. These additives will replace some of the water in the formulation.

The pH of the clear liquid facial cleanser of present invention, which may be in the form of a watery solution, a thick liquid, or a gel, may vary within the range of 4.5 to 6.5 and preferably from 5 to 6. Using the in vitro pretreated wool substrate described in the previous experiments to ascertain the effect of surfactant concentration on rinse base effectiveness, i.e. residual soap removal, a study of the effect of changing the rinse base pH was conducted. The surfactant and organic acid concentrations were held constant at 0.25% and 2% respectively.

The results shown in Table III indicate that increasing the pH of the rinse formulation decreases the efficiency of soap removal only slightly, from about 90% at pH 4.5 to 83% at pH 6.5. These slight losses in product performance can be made up by optimization of the surfactant and organic acid concentrations.

TABLE III

Effect of pH on Residual Soap Removal by a Rinse Formula

| Treatment* Removal | Percent Soap |
|---|---|
| pH 4.5 | 89.2 ± 2.34 |
| pH 5.0 | 90.5 ± 1.90 |
| pH 5.5 | 84.2 ± 0.79 |
| pH 6.0 | 82.9 ± 0.27 |
| pH 6.5 | 83.1 ± 4.41 |

*All treatment solutions contained 0.25% Tergitol and 2.0% citric acid

Using the in vitro technique, efficacy of facial rinse skin cleanser clinical formulas in removing residual soap was evaluated. Formulas 'A' and 'C' contained 2.0% citric acid, were adjusted to pH 5.0, and had 1% and 6% tergitol respectively. Formula 'B' contained 300 ppm hard water only. The results of the study are shown in Table IV, compared to the appropriate controls.

TABLE IV

Efficacy of Facial Rinse Clinical Formulas in Removing Residual Soap

| Treatment | Percent Soap Removal |
| --- | --- |
| Product A (1% Tergitol)* | 92.2 ± 1.05 |
| Product B (Hard Water) | 13.7 ± 0.77 |
| Product C (6% Tergitol)* | 98.1 ± 0.30 |
| Control 1 (1% Tergitol, 2% Citric Acid) | 92.9 ± 1.66 |
| Control 2 (Hard Water) | 14.9 ± 0.66 |

*These formulas contained 2.0% citric acid, adjusted to pH 5.0

The results of the soap removal study agree with the formula composition, i.e. hard water ('B') removed the least soap (13.7%), the 1% Tergitol formula ('A') removed 93%, and the 6% formula ('C') removed 98% of the residual soap from the wool keratin samples. The results are in agreement with those of the clinical study, where significant differences were found between the control and the test products.

In vitro evaluations further show that the optimum formula ingredient levels for removing residual soap with a pH 6.0 formula were 0.54% citric acid and 0.77% Tergitol 15-S-9, exhibiting a 99% soap removal.

The coaction of the nonionic surfactant, the citric acid and the pH provides a facial skin cleanser which optimizes residual soap removal, and provides a smooth, soft moisturized feel to the skin. The present novel facial cleanser has overcome the dry, tight, rough and flaky sensations after washing with soap. Test data has shown that compositions containing the combination of 0.5% citric acid and 0.5% nonionic surfactant removes about 91% soap, whereas citric acid compositions remove about 10% soap, 1% Tergitol (nonionic) removes about 77% soap, and the control (water only) removes 33.9% soap. Accordingly, the criticality of the ingredients and the specificity of each ingredient is necessary in the formulation of the present novel facial skin cleanser/skin conditioner which can also be used as a preshave and post-shave skin conditioner.

The skin cleansers of the present invention are generally prepared by mixing the thickening agent, when used, with water until hydrated, then adding the nonionic surfactant and the organic acid and/or the sodium salt thereof, such as the citric acid and/or sodium citrate, in the water to form a uniform aqueous thickened solution, adding an aqueous solution of the preservative system to said aqueous solution with mixing, mixing until a homogeneous thick liquid or gel is formed, and adjusting the pH if necessary.

The skin cleansers of present invention are clear, colorless, liquids which can be poured from any suitable container. The thin or watery liquids flow rapidly like water, when poured. The viscous or thick liquids flow slowly when poured. The gel also flows slowly when poured.

This product is preferably used after washing the face and/or body with soap and water. After the soap lather is rinsed away, the cleanser of present invention is applied to the face and/or body by any suitable means. For example, the face is swabbed, using a cotton ball saturated with the facial cleanser, or the liquid is poured into the hands and rubbed onto the face. The face is rinsed with water, and dried using a towel.

The following examples merely illustrate the invention, but it is understood that the invention is not limited thereto. All amounts of various ingredients in the examples and elsewhere in the specification are by weight unless otherwise specified.

EXAMPLES 1 and 2

Facial Cleanser/Skin Conditioner

| Ingredients | 1 % | 2 % |
| --- | --- | --- |
| Tergitol 15-S-9 | 1 | 6 |
| Sodium citrate | 2.0 | 2.0 |
| Water | 97.0 | 92.0 |
| pH | 5 | 5 |

These products are prepared by adding the Tergitol and the sodium citrate to the water and mixing until a uniform solution is obtained.

An in vivo (clinical) study was run with both examples to test the skin feel after swabbing the face with each formulation subsequent to washing with soap and rinsing off the lather with 300 ppm (hard) water. Panelists reported that both products 1 and 2 left the facial skin feeling significantly less dry, tight and rough, and appearing less flaky after washing with soap compared with a 300 ppm hard water rinse. After using these products the facial skin felt significantly softer and smoother and more moisturized after washing with soap compared With a 300 ppm hard water rinse. Examples 1 and 2 can also be used as a post-shave cleanser/conditioner.

Examples 1 and 2 were also used as a pre-shave/skin conditioner to prevent or reduce the deposition of shaving cream soap on the skin and thereby preventing or reducing skin irritation due to soap, such as tightness, roughness and dryness.

In vitro studies have demonstrated that these formulations will reduce the deposition of up to 33% of soap from the shave cream on wool fabric.

EXAMPLE 3

Gel Facial Cleanser

| Ingredient | % |
| --- | --- |
| Sterile Deionized Water | 95.9% |
| Tergitol 15-S-9 | 2.0% |
| Carbopol 941 | 1.0% |
| Citric Acid | 0.5% |
| DMDM Hydantoin | 0.3% |
| Ethylene diamine tetra acetic acid (EDTA) | 0.3% |
| | 100.0% |

The gel facial cleanser is a clear, colorless gel, which flows slowly when poured.

This product is prepared by dissolving Carbopol (Carbomer 941) in deionized water then adding Tergitol (Pareth 15-9) and citric acid and mixing until a uniform thickened aqueous solution is obtained. DMDM hydantoin (Gludent-Glyco) and EDTA are added to the solution and mixed until completely dissolved. A gel is formed as the pH is adjusted to 6.0 with sodium hydroxide.

In vivo, when panelists used the cleanser after facial washing, they reported that their skin felt less tight, dry and rough as well as softer, smoother and more moisturized compared with washing with soap. The cleanser contains a low level of a mild non-ionic detergent.

This formulation can also be used as a pre-shave/skin conditioner to reduce the deposition of shaving cream soap on the skin, as well as a post-shave cleanser/conditioner to effect a softer, smoother feel to the skin.

EXAMPLE 4

Gel Facial Cleanser 1.0% Tergitol 15-S-9
0.6% Carbopol 940 (thickener)
0.3% DMDM Hydantoin
0.3% EDTA
0.1% Citrate
97.7% Sterilized Deionized Water
pH adjusted to 6.0 with sodium hydroxide This gel is prepared in accordance with the procedure set forth in Example 3.

This product exhibits the same conditioning properties of smoothness, softness and moisturizing when applied as a cleanser during washing or after shaving with soap.

The aforedescribed examples may be modified by the substitution of other nonionic surfactants for the Tergitol 15-S-9, such as Tween 20, Tween 80 and Neodol 25-7 (Pareth 25-7-Shell), without adversely affecting the compositions. Likewise, PEG-distearate may be substituted for the Carbopol thickening agent to form a thick liquid. Also, the citric acid or citrate may be replaced by glutaric, succinic or acetic acid and/or the sodium or triethanolamine salts thereof.

It is understood that the foregoing detailed description is given merely by way of illustration and that variations may be made therein without departing from the spirit of the invention.

We claim:

1. A liquid skin cleanser and conditioner composition consisting essentially of a major amount of about 84–98% by weight of water, about 0.25–6% by weight of a nonionic surfactant as the sole surfactant, about 0.05–5% by weight of an organic acid having a pKa from 4.5–6.5, said composition adjusted to have a pH of 4.5–6.5, whereby said composition is effective in reducing the deposition of soap and surfactant residue on the skin prior to such skin being washed with a soap or surfactant containing material or in removing soap and surfactant residue from skin after such skin has been washed with a soap or surfactant containing material and simultaneously conditions the skin to feel soft, smooth and moisturized.

2. The composition according to claim 1, wherein the nonionic surfactant is a water soluble ethoxylated nonionic surfactant selected from the group consisting of a polyglycol ether condensate of a $C_8$–$C_{20}$ fatty alcohol or mixture of fatty alcohols with an average of 5 to 30 moles of ethylene oxide, and a polysorbate containing 20 moles of ethylene oxide.

3. A skin cleanser and conditioner composition consisting essentially of a major amount of about 84–98% by weight of water, about 0.25–6% by weight of a nonionic surfactant as the sole surfactant, about 0.05–5% by weight of an organic acid having a pKa from 4.5–6.5, said composition having a pH of 4.5–6.5, and a preservative system of 1,3-dimethyl-5,5 dimethyl hydantoin and disodium ethylene diaminetetraacetate, in equal amounts, whereby said composition is effective in reducing the deposition of soap and surfactant residue on the skin prior to such skin being washed with a soap or surfactant containing material or in removing soap and surfactant residue from skin after such skin has been washed with a soap or surfactant containing material and simultaneously conditions the skin to feel soft, smooth and moisturized.

4. The composition according to claim 3, additionally containing about 0.1–4% by weight of a thickening agent selected from the group consisting of a diester of stearic acid and polyoxyethylene, and a polyacrylic acid resin.

5. The composition according to claim 4, in the form of a clear gel containing about 0.1–2% by weight of a polyacrylic acid resin.

6. The composition according to claim 4, in the form of a thick liquid containing about 2–4% by weight of a diester of stearic acid and polyoxyethylene.

7. The composition according to claim 2, wherein the nonionic surfactant constitutes 0.7–6% by weight of the composition having a pH of 5–6.

8. The composition according to claim 7, wherein the nonionic surfactant is a polyethylene glycol ether of a mixture of synthetic $C_{11}$–$C_{15}$ fatty alcohols with an average of 9 moles of ethylene oxide.

9. The composition according to claim 7, wherein the nonionic surfactant is a polyethylene glycol ether of a mixture of synthetic $C_{12}$–$C_{15}$ fatty alcohols with an average of 7 moles of ethylene oxide.

10. The composition according to claim 7, wherein the nonionic surfactant is a mixture of laurate or oleate esters of sorbitol and sorbitol anhydrides condensed with about 20 moles of ethylene oxide.

11. The composition according to claim 2 wherein the nonionic surfactant constitutes about 0.5–2.0% by weight of the composition.

12. The composition according to claim 1, wherein the organic acid is citric acid and constitutes about 0.1–2.0% by weight of the composition.

13. The composition according to claim 3, wherein each of the ingredients in the preservative system constitutes about 0.3% by weight of the composition.

14. The composition according to claim 2, consisting of 0.77% by weight of nonionic surfactant, 0.54% by weight citric acid, and having a pH of 6.

15. A liquid skin cleanser and conditioner composition consisting essentially of a major amount of about 84–98 wt % by weight of water, about 0.25–6% by weight of a nonionic surfactant as the sole surfactant, about 0.05–5% by weight of an organic acid having a pKa from 4.5–6.5, said composition adjusted to have a pH of 4.5–6.5 and about 0.1–4% by weight of a thickening agent selected from the group consisting of a diester of stearic acid and polyoxyethylene and a polyacrylic acid; resin whereby said composition is effective in reducing the deposition of soap and surfactant residue on the skin prior to such skin being washed with a soap or surfactant containing material or in removing soap and surfactant residue from skin after such skin has been washed with a soap or surfactant containing material and simultaneously conditions the skin to feel soft, smooth and moisturized.

16. The composition according to claim 5, wherein the gel consists of 2% by weight nonionic surfactant, 1% by weight polyacrylic acid resin, 0.5% by weight citric acid, 0.3% by weight DMDM hydantoin, 0.3% by weight ethylene diamine tetra acetic acid and 95.9% by weight deionized water, having a pH of 6.

17. A clear liquid skin cleanser and conditioner composition that reduces the deposition of soap and surfactant on the skin, removes soap and surfactant residue previously deposited on the skin, and simultaneously conditions the skin to feel soft, smooth and moisturized, said composition consisting essentially of major amount of about 84–98% by weight of water, about 0.25%–6% by weight of a nonionic surfactant as the sole surfactant, about 0.05%–5% by weight of a monovalent cation salt of an organic acid having a pKa from 4.5–6.5 or a mixture of said acid and said salt, said composition having a pH of 4.5–6.5 and about 0.1–4% by weight of a thickening agent selected from the group consisting of a diester of stearic acid and polyoxyethylene and a polyacrylic acid.

18. The composition according to claim 1, in the form of a liquid pre-shave/skin conditioner to reduce the deposition of shaving cream soap on the skin.

19. The composition according to claim 5, in the form of a gel pre-shave/skin conditioner for reducing the deposition of shaving cream soap on the skin and preventing or reducing skin irritation due to the soap.

20. The composition according to claim 6, in the form of a thick liquid pre-shave/skin conditioner to reduce both the deposition of shaving cream soap on the skin, and the skin irritation due to the soap.

21. The composition according to claim 1, in the form of a facial rinse cleanser and conditioner.

22. The composition according to claim 21, in the form of a liquid post-shave cleanser and conditioner.

23. The composition according to claim 5, in the form of a gel facial cleanser and conditioner.

24. The composition according to claim 23, in the form of a gel post-shave cleanser and conditioner.

25. The composition according to claim 6, in the form of a thick liquid facial cleanser and conditioner.

26. The composition according to claim 25, in the form of a thick liquid post-shave cleanser and conditioner.

27. The composition according to claim 1 wherein the organic acid is selected from the group consisting of citric acid, acetic acid, succinic acid and glutaric acid.

28. The composition according to claim 1 wherein the organic acid is citric acid and constitutes about 0.1–2.0% by weight of the composition.

29. A clear liquid skin cleanser and conditioner composition that reduces the deposition of soap and surfactant on the skin, removes soap and surfactant residue previously deposited on the skin, and simultaneously conditions the skin to feel soft, smooth and moisturized, said composition consisting essentially of a major amount of about 84–98% by weight of water, about 0.25%–6% by weight of a nonionic surfactant as the sole surfactant, about 0.05%–5% by weight of a monovalent cation salt of an organic acid having a pKa from 4.5–6.5 or a mixture of said salt and an organic acid having a pKa of from 405–6.5, said composition having a pH of 4.5–6.5.

30. The composition according to claim 29, wherein the nonionic surfactant is a water soluble ethoxylated nonionic surfactant selected from the group consisting of a polyglycol ether condensate of a $C_8$–$C_{20}$ fatty alcohol or mixture of fatty alcohols with an average of 5 to 30 moles of ethylene oxide, and a polysorbate containing 20 moles of ethylene oxide.

31. The composition according to claim 29, additionally containing a preservative system of 1,3-dimethylol-5,5 dimethyl hydantoin and disodium ethylene diaminetetraacetate, in equal amounts.

32. The composition according to claim 31, additionally containing about 0.1–4% by weight of a thickening agent selected from the group consisting of a diester of stearic acid and polyoxyethylene, and a polyacrylic acid resin.

33. The composition according to claim 32, in the form of a clear gel containing about 0.1–2% by weight of a polyacrylic acid resin.

34. The composition according to claim 32, in the form of a thick liquid containing about 2–4% by weight of a diester of stearic acid and polyoxyethylene.

35. The composition according to claim 30, wherein the nonionic surfactant constitutes 0.7%–6% by weight of the composition having a pH of 5–6.

36. The composition according to claim 35, wherein the nonionic surfactant is a polyethylene glycol ether of a mixture of synthetic $C_{11}$–$C_{15}$ fatty alcohols with an average of 9 moles of ethylene oxide.

37. The composition according to claim 35, wherein the nonionic surfactant is a polyethylene glycol ether of a mixture of synthetic $C_{12}$–$C_{15}$ fatty alcohols with an average of 7 moles of ethylene oxide.

38. The composition according to claim 35, wherein the nonionic surfactant is a mixture of laurate or oleate esters of sorbitol and sorbitol anhydrides condensed with about 20 moles of ethylene oxide.

39. The composition according to claim 30, wherein the nonionic surfactant constitutes about 0.5–2% by weight of the composition.

40. The composition according to claim 31, wherein each of the ingredients in the preservative system constitutes about 0.3% by weight of the composition.

41. The composition according to claim 30, consisting of 1% nonionic surfactant, 2% sodium citrate, and having a pH of 5.

42. The composition according to claim 33, wherein the gel consists of 1% nonionic surfactant, 0.6% by weight polyacrylic acid resin, 0.1% by weight sodium citrate, 0.3% by weight DMDM hydantoin, 0.3% by weight ethylene diamine tetracetic acid and 97.7% deionized water, having a pH of 6.

43. The composition according to claim 29 in the form of a liquid preshave/skin conditioner to reduce the deposition of shaving cream soap on the skin.

44. The composition according to claim 33 in the form of a gel preshave/skin conditioner for reducing the deposition of shaving cream soap on the skin and preventing or reducing skin irritation due to the soap.

45. The composition according to claim 34 in the form of a thick liquid preshave/skin conditioner to reduce both the deposition of shaving cream soap in the skin, and the skin irritation due to the soap.

46. The composition according to claim 29 in the form of a facial rinse cleanser and conditioner.

47. The composition according to claim 46 in the form of a liquid post-shave cleanser and conditioner.

48. The composition according to claim 33 in the form of a gel facial cleaner and conditioner.

49. The composition according to claim 48 in the form of a gel post-shave cleanser and conditioner.

50. The composition according to claim 34, in the form of thick liquid facial cleanser and conditioner.

51. The composition according to claim 50 in the form of a thick liquid post-shave cleanser and conditioner.

52. The composition according to claim 29 wherein the organic acid is citric, acetic, succinic or glutaric acid or a combination thereof and the monovalent cation salt of the organic acid is the monovalent cation salt of citric, acetic, succinic or glutaric acid or a combination thereof.

53. The composition according to claim 29 wherein the organic acid is citric acid, the monovalent cation salt of the organic acid is sodium citrate, and said mixture constitutes about 0.1–2.0% by weight of the composition.

* * * * *